US006399056B1

(12) United States Patent
Ono et al.

(10) Patent No.: US 6,399,056 B1
(45) Date of Patent: Jun. 4, 2002

(54) MICROORGANISM

(75) Inventors: Kotaro Ono, Fukui; Noriaki Yamanaka, Osaka; Katsuyo Watanabe, Tokyo, all of (JP)

(73) Assignee: Washi Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/485,939

(22) PCT Filed: Sep. 3, 1998

(86) PCT No.: PCT/JP98/03941

§ 371 (c)(1),
(2), (4) Date: Feb. 18, 2000

(87) PCT Pub. No.: WO99/11756

PCT Pub. Date: Mar. 11, 1999

(30) Foreign Application Priority Data

Sep. 3, 1997 (JP) .............................................. 9-237974
Mar. 6, 1998 (JP) .......................................... 10-054882
May 6, 1998 (JP) .......................................... 10-123426

(51) Int. Cl.[7] .............................................. A01N 63/00
(52) U.S. Cl. ............... 424/93.462; 424/520; 435/252.1; 435/252.5; 435/839
(58) Field of Search ........................... 424/93.462, 520; 435/252.1, 252.5, 839

(56) References Cited

U.S. PATENT DOCUMENTS 5,155,041 A * 10/1992 Bok et al. ................ 435/252.1

FOREIGN PATENT DOCUMENTS

| JP | 63-273470 | 11/1988 |
| JP | 3-216158 | 9/1991 |
| JP | 4-166080 | 6/1992 |

OTHER PUBLICATIONS

Pelczar, M.J. et al. Microbiology Concepts and Application. 1993. McGraw Hi, Inc. 189–190.*
ATCC Bacteria and BActeriophages, 1996. , p. 57 entry #6051.*
Sneath, P.A. et al (eds.). Bergey's Manual of Systematic Bacteriology vol. 2. 1987, Williams and Wilkins,, Baltimore, pp. 1108, 1130.*
Gordon, R.E. et al. The Genus BAcillus. ARS, USDA, WAshington, D.C., 1973. pp. 36–41.*

* cited by examiner

*Primary Examiner*—Christopher R. Tate
*Assistant Examiner*—Kailash C. Srivastava
(74) *Attorney, Agent, or Firm*—Jordan and Hamburg LLP

(57) ABSTRACT

A novel microorganism such as a Bacillus sp. OYK-01-600 (FERM BP-6394) which has no induction period, immediately undergoes exponential growth, and is nonhemolytic. The bacteria have antimicrobial activities against toxic bacteria such as *Staphylococcus aureus*, including methicillin-resistant *Staphylococcus aureus*, pathogenic *Eschericia coli* including O-157, *Legionella pneumophila*, and *Klebsiella pneumoniac*. The increased growth rate can inhibit bacteria which emit an ofensive odor and many noxious infection bacteria.

2 Claims, 1 Drawing Sheet

MICROORGANISM

TECHNICAL FIELD

The present invention relates to a novel nonhemolytic microorganism and to its utilization, and more particularly to a novel microorganism which expresses not only high antimicrobial activity against those noxious bacteria which give off offensive odors in the course of proliferation (for example, *Staphylococcus aureus, Klebsiella neumoniae,* etc.) and, as such, is capable of getting rid of the malodor originating from effluent treatment and facilities, but also high antimicrobial activity against other toxic bacteria (for example, meticillin-resistant *Staphylococcus aureus,* pathogenic *Escherichia coli* O-157, *Legionella pneumophila,* etc.), thus finding application in a broad spectrum of uses and to the utilization thereof.

It should be understood that the antimicrobial activity of the novel microorganism according to the present invention is derived not only from the extracellular and intracellular secretions of this novel microorganism but also from the following mechanism.

The novel microorganism of the present invention proliferates at an unusually high growth rate. Thus, at an incubation temperature of 20~40° C., it multiplies from an initial population of $10^3$ cells/g (ml) to a population $10^6$ cells/g (ml) in about 2 hours and further to $10^8$ cells/g (ml) within 6 hours. Whereas growth of ordinary or adventitious bacteria occurs only after the so-called induction period, that is to say an acclimatization period (the time which a microorganism placed in a new environment requires for its being acclimatized to the new environment) of about 6 hours, the novel microorganism of the present invention has substantially no "induction period" as mentioned above but undergoes cell division and multiplies rapidly in an explosive manner after initiation of culture. As the microorganism of the present invention avariciously digests and assimilates available nutrients and grows explosively while said other adventitious bacteria are still in the induction period of growth, proliferation of the adventitious bacteria is inhibited and the above-mentioned antimicrobial activity against such adventitious bacteria is expressed. Thus, this novel microorganism having substantially no induction period and starting to grow immediately after commencement of culture inhibits growth of noxious bacteria.

BACKGROUND TECHNOLOGY

Recent years have witnessed what may be called the heyday of the technology utilizing microorganisms, inclusive of the waste water treatment technology. While a large variety of microorganisms are utilized in waste water treatment, the following can be reckoned as representative organisms. Thus, as the bacteria used, Zooglea, Sphaerotilus, etc. can be mentioned; as the protozoa used, Rhizopoda, Mastigophora, Ciliata, etc. can be mentioned; and as the algae, Cyanophyceae, Chlorophyceae, Diatomeae, etc. can be mentioned.

These microorganisms are capable of decomposing organic matter and some of inorganic matter but tend to induce, in decomposing them, the production of malodors (ammonia odor, hydrogen sulfide odor) and malodor-emitting substances, and the malodors generated from waste water treatment plants have frequently been reported as a social problem. Thus, even if the decomposition of organic and inorganic substances were efficiently achieved, the malodors originating from such treatment facilities remained to be dealt with. Particularly, the active sludge formed in a sedimentation tank becomes progressively anaerobic and, as anaerobic bacteria grow, they emit a copious malodor. In the course of recycling such an active sludge to the aeration tank, a considerable spread of noxious odor drifts around the effluent treatment plant.

With the genesis of the foregoing problem by way of background, the inventors of the present invention explored earnestly for a new useful microorganism and ultimately succeeded in isolating from soil a novel useful microorganism which does not cause evolution of the malodors of hydrogen sulfide, methylmercaptan, etc. in the decomposition of organic matter and has antimicrobial activity not only against the bacteria which grow with emission of malodors, such as *Staphylococcus aureus* and *Klebsiella pneumoniae,* but also against meticillin-resistant *S. aureus,* pathogenic *E. coli.* O-157, *Legionella* spp., *Pseudomonas aeruginosa* and so forth. They found, also, that this novel microorganism can be utilized in a large variety of uses and have ultimately developed the present invention.

DISCLOSURE OF INVENTION

The novel microorganism of the present invention is a nonhemolytic *Bacillus subtilis*-related microorganism which is not less than 4 times as large as the type culture strain of *Bacillus subtilis* (IFO 3134) in cell volume and grows substantially without an induction period in an early stage of culture, for example showing an increase in population from an initial count of $10^3$ cells/ml to a count of not less than $10^7$ cells/ml in 4 hours when it is subjected to nutrient broth shake culture at 37° C. As the synergism of those characteristics, the metabolic energy generated by its growth reaches not less than $1 \times 10^4$ times as compared with said type culture strain of *B. subtilis.* As such, this microorganism expresses antimicrobial activity against *Staphylococcus aureus, Klebsiella pneumoniae,* meticillin-resistant *S. aureus,* pathogenic *E. coli* O-157, *Legionella* spp., *Pseudomonas aeruginosa,* Fusarium spp., koji mold (*Aspergillus oryzae*), blue mold (Penicillium spp.), Trichophyton spp., and Rhyzopus spp.

As examples of the *Bacillus subtilis*-related microorganism, which is the novel microorganism of the present invention, the following OYK strains (deposited under the international convention with Patent Microorganism Deposit Center, National Institute of Bioscience and Human Technology, Agency of Industrial Science and Technology, the Ministry of International Trade and Industry, Japan) can be mentioned.

(1) Bacillus sp. OYK-01-600 (FERM BP-6394),
(2) Bacillus sp. OYK-03-600 (FERM BP-6395),
(3) Bacillus sp. OYK-04-000 (FERM BP-6396).

In the following description, each of OYK-01-600, OYK-03-600 and OYK-04-000 will be referred to briefly as the OYK strain.

The OYK strain digests protein and grows luxuriantly. Moreover, the OYK strain is characterized in that it does not produce hemolysin and, therefore, is highly safe to the human being. The safety of the strain has been confirmed by administering it to animals by four routes, namely intravenous, airway, oral and percutaneous.

The OYK strain is comparatively large in size among various strains of *B. subtilis*. For example, it is about 4 times (by volume) larger than the type culture strain of *Bacillus subtilis* [IFO 3134 (0.4~0.6×1.5~3.2 μm)]. Moreover, the OYK strain has a greater initial growth potential after the start of culture and thereby produces higher metabolic energies (whereas the type culture strain multiplies only 6-fold in 4 hours after the start of culture, the OYK strain grows as many as about 80,000 times). Moreover, being a facultative anaerobe, the strain is able to grow actively under both aerobic and anaerobic conditions. Therefore, it increases the temperature of organic wastes quickly in the production of a compost to promote growth of the thermophilic actinomyces and hyphomyces and thereby reduce the compost ripening time and give rise to a full-ripe compost.

BEST MODE FOR CARRYING OUT THE INVENTION

Figure 1:
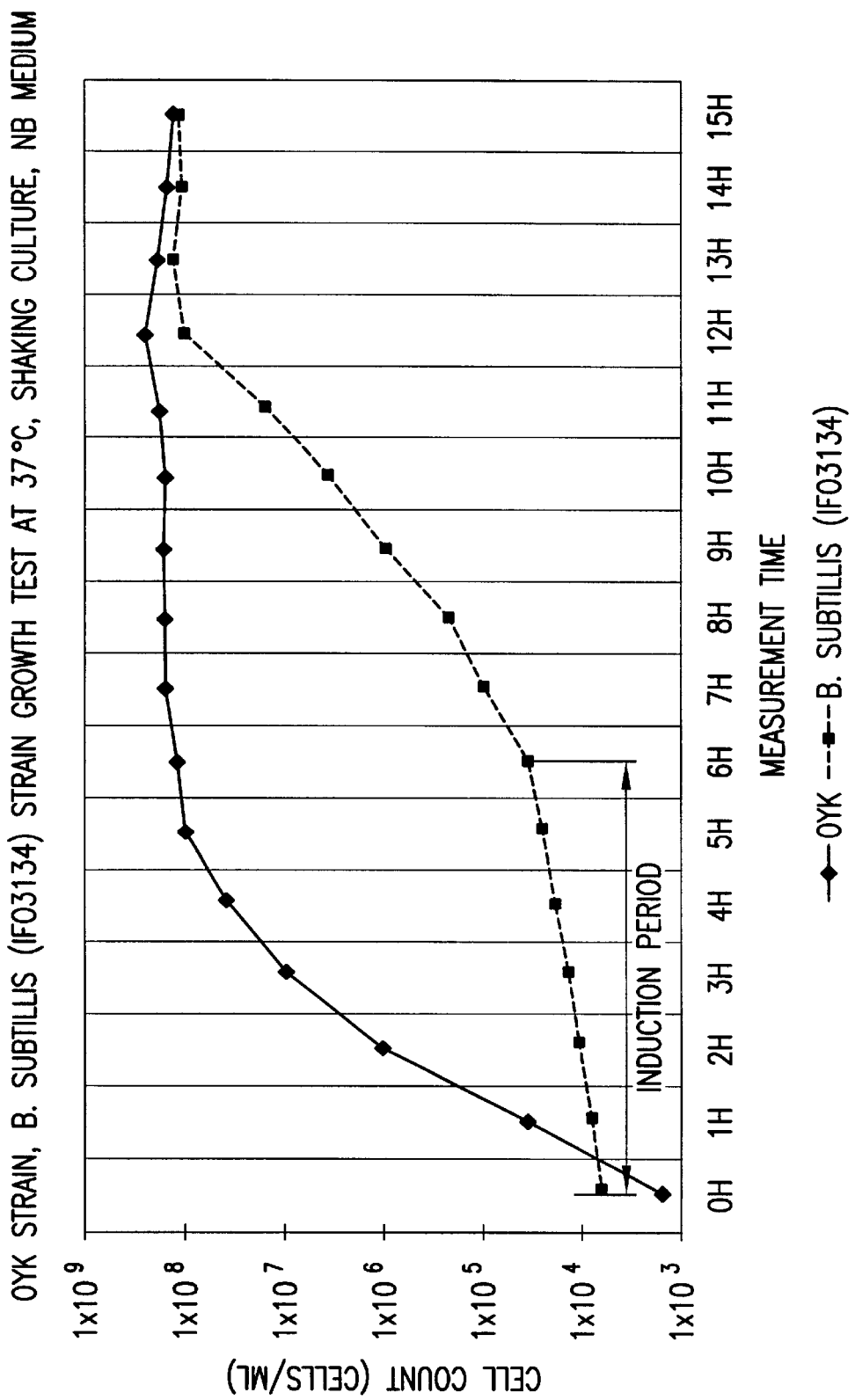
FIG. 1 is a diagrammatic representation showing the relative growth speeds of the OYK microorganism and the type culture strain of *B. subtilis*.

The present invention is now described by way of examples. It should be understood that these examples are merely illustrative and by no means limitative of the scope of the invention.

A. Screening for Novel Microorganisms

Three strains of microorganisms having antimicrobial activity against bacteria whose growth is accompanied by emanation of malodors were isolated from the soil. Soil microorganisms are generally considered to be only sparingly toxic and the above 3 OYK strains isolated from the soil may also be considered safe (benign) to the human body.

B. Identification of the Strains

The microbiological characteristics of the strains isolated and screened by the present inventors were differentiated according to the following literature (1) and (2).
(1) Bergey's Mannual of Determinative Bacteriology, Vol 2 (1986), Williams & Wilkins, U.S.A.
(2) R. E. Gordon, W. C. Haynes, C. H. Pang. (1973). The Genus Bacillus. Agr. Handbook No. 427, United States Department of Agriculture, Washington D.C.

Tests were performed by the under-mentioned procedures.
1. Morphologic Characters (Results are Shown Below in Table 1)
   (1) Cell Size
   (2) Cell Form
   (3) Polymorphism The observation is made using an electron microscope at ×5,000–30,000 magnification. Each test strain is cultured on an agar plate at 37° C.×1 day and the colony formed is harvested. The broth agar medium used is composed of meat extract 5 g, peptone 10 g, NaCl 5 g, agar 15 g and distilled water 1,000 ml.
   (4) Motility
   1) Flagella are strained by the method of Nishizawa and Sugawara and observed with an electron microscope (×10,000). The first solution is composed of tannic acid 100 ml, ferric chloride solution JP 1.5 ml, formalin 2 ml, 1% NaOH 1 ml, and distilled water 100 ml, and the second solution is composed of silver nitrate 2 g, aqueous ammonia JP q.s., and distilled water 100 ml.
   2) Stab culture is performed using a semi-fluid broth agar medium for stab culture and the evaluation is made according to the turbidity of the entire medium. The semi-fluid both agar medium is composed of meat extract 5 g, peptone 10 g, NaCl 5 g, agar 5 g and distilled water 1,000 ml.
   (5) Sporulation
   1) The culture obtained by shake culture on broth agar is heated at 85° C.×15 minutes and transferred to a broth agar plate by the spread-plating dilution technique and the evaluation is made according to the formation of colonies. The broth agar medium used is composed of meat extract 3 g, peptone 5 g and distilled water 1,000 ml.
   2) Spores are stained by the method of Wirtz (modified Schaeffer-Fulton method) and the evaluation is made according to red staining for cells and green staining for spores. The red color of cells is developed with 0.5% aqueous safranine and the green color of spores is developed with 5% aqueous malachite green.
   (6) Sporangium Form
   (7) Spore Form
   (8) Position of Spore Formation
   (9) Spore Size Spores are stained by the method of Writz (modified Schaeffer-Fulton method) and observed with an electron microscope at ×5,000 magnification. The test strain is cultured on a broth agar plate at 37° C.×1 day and harvested from the cold colonies stored in a refrigerator at 4° C. for 1 day.
   (10) Gram-stain The modified Hucker method is used. The positive test is a violet stain with crystal violet and the negative test is a red stain by counter staining with safranin red. The test strain is cultured on a broth agar plate at 37° C.×1 day and harvested from the colony formed.
   (11) Acid-fastness The Ziiehl-Neeisen staining method is used. The positive test is a red stain with fuchsine-phenol and the negative test is a green stain by counter staining with malachite green. The test strain is cultured on a broth agar plate at 37° C.×1 day and harvested from the colony formed.

TABLE 1

Morphological characters

| Morphological observation parameters | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| (1) Cell size | 0.7–0.9 × 2.5–5.1 μm | 0.7–0.9 × 2.5–5.1 μm | 0.7–0.9 × 2.5–5.1 μm |
| (2) Cell form | Rod | Rod | Rod |
| (3) Cell polymorphism | None | None | None |
| (4) Motility | Motile | Motile | Motile |
| (5) Sporulation | Spore-forming | Spore-forming | Spore-forming |
| (6) Sparangium form | Non-distending | Non-distending | Non-distending |
| (7) Spore form | Oblong | Oblong | Oblong |
| (8) Position of spore formation | Central - subterminal | Central - subterminal | Central - subterminal |
| (9) Spore size | 0.8–1.0 × 1.5–1.8 μm | 0.8–1.0 × 1.5–1.8 μm | 0.8–1.0 × 1.5–1.8 μm |
| (10) Gram-stain | Positive | Positive | Positive |
| (11) Acid-fastness | Positive | Positive | Positive |

2. Cultural Characters on Various Media (Results are Shown below in Tables 2 and 3)
   (1) Broth Agar Plate Culture
   [Medium composition] (in 1,000 ml of distilled water) Meat extract 5 g, sodium chloride 5 g, peptone 10 g, agar 15 g (pH 7.0±0.1).
   [Cultural conditions]
   The medium is set in sterilized dishes and the test strain is streak-cultured. 37° C.×3 days.
   (2) Broth Agar Slant Culture
   [Medium composition] (in 1,000 ml of distilled water)
   The same as above

[Cultural conditions]

The medium is set in inclined position in sterilized test tubes and the test strain is streak-cultured on the medium. 37° C.×3 days.

(3) Liquid Broth Culture

[Medium composition] (in 1,000 ml of distilled water) Meat extract 5 g, sodium chloride 5 g, peptone 10 g (pH 7.0±0.1).

[Cultural conditions]

The medium is dispensed into sterilized test tubes and the test strain is suspended in the medium. 37° C.×3 days, under shaking at 170 cycles/min.

(4) Gelatin Stab Culture

[Medium composition] (in 1,000 ml of distilled water) Meat extract 5 g, sodium chloride 5 g, peptone 10 g, gelatin 15 g (pH 7.0±0.1).

[Cultural conditions]

The medium for stab culture is set in sterilized test tubes and the test strain is stab-cultured. 25° C.×7 days.

[Observation parameters other than growth]

Liquefaction of gelatin by proteolysis.

(5) Litmus Milk Liquid Culture

[Medium composition] (in 1,000 ml of distilled water) Skim milk power 110 g, litmus solution q.s. (pH 7.0±0.1).

[Cultural conditions]

The medium is dispensed into sterilized test tubes and the test strain is suspended in the medium. 25° C.×14 days. Stationary culture.

[Observation parameters other than growth]

Coagulation of cow's milk due to the acid produced by decomposition of lactose

Coagulation of cow's milk due to the rennin produced by decomposition of lactose Precipitation of cow's milk serum due to the rennin produced by decomposition of lactose

TABLE 2

Cultural characters on various media

| Cultural characters examined | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| (1) Broth agar plate culture, 37° C. × 3 days | The 3 mutant strains showed more or less similar cultural characters. | | |
| Growth | Very rapid, growing to attain a diameter of 2–3 mm in 1 day and 4–6 mm in 2 days. | | |
| Surface | Translucent, with slightly granulose irregularities | | |
| Color | Cream-like milk white | | |
| Size | 6–8 mm in diameter | | |
| Gloss | Slightly glistening | | |
| Form | Circular | | |
| Elevation | Flat but the mycelial pad is heavily thick | | |
| Margin | Not an entire but a fimbriated or sinuated margin | | |
| Pigment production | None | | |

TABLE 3

| Cultural characters examined | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| (2) Broth agar slant culture, 37° C. × 3 days | The 3 mutant strains showed more or less similar cultural characters. | | |

TABLE 3-continued

| Cultural characters examined | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| Growth | Luxuriant, spreading well on the slant | | |
| Surface | Translucent, with slightly granulose irregularities | | |
| Color | Cream-like milk white | | |
| Gloss | Slightly glistening | | |
| Form | Flat but the mycelial pad is heavily thick | | |
| (3) Liquid broth culture, 37° C. × 3 days | | | |
| Turbidity | High | High | High |
| Surface growth | Profuse and punctate | Profuse and punctate | Profuse and punctate |
| Sediment | Moderate | Profuse | Profuse |
| (4) Gelatin stab culture, 25° C. × 7 days | The 3 mutant strains showed more or less similar cultural characters. | | |
| Growth | Luxuriant | | |
| Liquefaction | A 1.5 cm-deep white opaque liquefied layer from surface of medium | | |
| (5) litmus milk liquid culture, 25° C. × 14 days | | | |
| Production of acid | None | None | None |
| Coagulation | Positive | Positive | Positive |
| Separation of milk serum | Positive | Positive | Positive |

3. Physiological Characters (1) (Results are Shown below in Table 4)

(1) Reduction of Nitrate

[Medium composition] (in 1,000 ml of distilled water) Potassium nitrate 1 g, peptone 5 g.

[Cultural conditions]

The medium is dispensed into sterilized test tubes and a loopful of the test organism is suspended in the medium. 37° C.×5 days, under shaking at 170 cycles/min.

[Observation parameter]

Detection of nitrite: 1 ml of α-naphthylamine solution and 1 ml of sulfanillic acid solution are thoroughly mixed with the medium. Positive test: a pink-red color.

(2) Denitrification Reaction

[Medium composition] (in 1,000 ml of distilled water)

1) Sodium nitrate 10 g, meat extract 5 g

2) Meat extract 5 g.

[Cultural conditions]

The above media 1 and 2 are respectively dispensed into 2 sterilized test tubes and a loopful of the test organism is suspended in the medium. In one of the two tubes, liquid paraffin is overlayed in a thickness of 1~2 cm. 37° C.×13 days. Stationary culture.

[Observation parameter]

Anaerobic growth in the presence of nitrate: the evaluation is made according to the degree of turbidity and gas production in 4 tubes with or without nitrate and liquid paraffin.

(3) VP Test

[Medium composition] (in 1,000 ml of distilled water) Peptone 5 g, potassium dihydrogenphosphate 5 g, glucose 5 g.

[Cultural conditions]

The medium is dispensed into sterilized test tubes and a loopful of the test organism is suspended in the medium. 37° C.×3 days, under shaking at 170 cycles/min.

[Observation parameter]

Acetylmethylcarbinol as a decomposition product of glucose: 0.6 ml of α-naphthol solution and 0.2 ml of 40% aqueous KOH solution are added to 1 ml of the culture. Positive test: a deep red color.

(4) MR Test

[Medium composition] (in 1,000 ml of distilled water) Peptone 5 g, potassium dihydrogenphosphate 5 g, glucose 5 g.

[Cultural conditions]

The medium is dispensed into sterilized test tubes and a loopful of the test organism is suspended in the medium. 37° C.×3 days, under shaking at 170 cycles/min.

[Observation parameter]

Production of acid due to decomposition of glucose: methyl red is dripped into 1 ml of the culture. Positive test: a red color. Negative test: a yellow color.

(5) Production of Indole

[Medium composition] (in 1,000 ml of distilled water) Peptone 10 g, sodium chloride 5 g.

[Cultural conditions]

The medium is dispensed into sterilized test tubes and a loopful of the test organism is suspended in the medium. 37° C.×3 days, under shaking at 170 cycles/min.

[Observation parameter]

Detection of indole: the ability to produce indole from the amino acid tryptophan. To the culture is added 1/5~1/10 of Kovac's reagent (shown below), and the tube is swirled vigorously and allowed to stand. The upper layer of the bilayers formed is observed. Positive test: a crimson color. Negative test: a yellow color.

<Kovac's Reagent> p-Dimthylaminobenzaldehyde 5 g, amyl alcohol 75 ml, concentrated hydrochloric acid 25 ml.

(6) Production of Hydrogen Sulfide

[Medium composition] (commercial TSI agar medium, in 1,000 ml of distilled water) Meat extract 5 g, glucose 1 g, sodium chloride 5 g, ferric citrate 0.2 g, peptone 15 g, sodium thiosulfate 0.2 g, lactose 10 g, Phenol Red 0.002 g, sucrose 10 g, agar 15 g.

[Cultural conditions]

The medium is set in a semi-slant position within sterilized test tubes and inoculated by stabbing into the substance of the medium and smearing on the slant surface. 37° C.×1 day.

[Observation parameter]

Detection of hydrogen sulfide: positive test: a black substance in a low position on the slant.

(7) Hydrolysis of Starch

[Medium composition] (in 1,000 ml of distilled water) Starch 2 g, meat extract 5 g, peptone 10 g, sodium chloride 5 g, agar 15 g.

[Cultural conditions]

The medium is set on sterilized dishes and streak culture is carried out. Room temperature ×5 days.

[Observation parameter]

Detection of starch: an iodine-potassium iodide solution (shown below) is dripped on the dish showing growth of the test organism. Positive test: disappearance of the deep purple color.

<Iodine-potassium iodide solution>Potassium iodide 5 g, iodine 4 g/200 ml (8) Liquefaction of Casein

[Medium composition] (in 1,000 ml of distilled water) Skim milk 2 g, agar 5 g.

[Cultural conditions]

The above medium components are independently sterilized, mixed and the mixture is set on sterilized dishes. Then, streak culture is performed. 37° C.×1 day.

[Observation parameter]

Casein residues: Positive test: a transparent zone about the streak.

(9) Utilization of Citric Acid

[Medium composition] (commercial CIT agar medium, in 1,000 ml of distilled water)

Dipotassium hydrogenphosphate 1 g, monoammonium hydrogenphosphate 1 g, sodium citrate 2 g, magnesium sulfate 0.2 g, sodium chloride 5 g, BTB 0.024 g, agar 15 g.

[Cultural conditions]

The medium is set on sterilized dishes and streak culture is performed. 37° C.×1~3 days.

[Observation parameter]

Growth by utilizing citric acid as a sole carbon source: Positive test: blue discoloration of the medium or growth of the organism.

(10) Pigment Production

[Medium composition] (in 1,000 ml of distilled water) Peptone 20 g, glycerin 10 g, $K_2SO_4$ 10 g, $MgCl_2$ 1.4 g, agar 15 g.

[Cultural conditions]

The medium is set on sterilized dishes and streak culture is performed. 25° C.×5 days.

[Observation parameter]

Production of pigments: Selective coloration of the medium around colonies indicates production of insoluble pigments, while coloration of the whole medium indicates production of soluble pigments.

(11) Urease

[Medium composition] (in 1,000 ml of distilled water) Urea 20 g, peptone 2 g, glucose 1 g, sodium chloride 5 g, potassium dihydrogenphosphate 2 g, 0.2% Phenol Red 6 ml, agar 15 g (Note: agar is autoclaved at 121° C.×15 min. and the other components are sterilized using a bacterial filter).

[Cultural conditions]

The medium is set in an inclined position within sterilized test tubes and smear culture is performed. 370° C.×1 day.

[Observation parameter]

Detection of ammonia: Positive test: the medium turns red.

(12) Oxidase

[Medium composition] (in 1,000 ml of distilled water) Meat extract 5 g, peptone 10 g, sodium chloride 5 g, agar 15 g.

[Cultural conditions]

The medium is set on sterilized dishes and streak culture is performed. 37° C.×1 day.

[Observation parameter]

Presence of cytochrome: A 1% aqueous solution of dimethyl-p-phenylenediamine is dripped on colonies on the plate. Positive test: the drip color turns pink and, then, black.

(13) Catalase

[Medium composition] (in 1,000 ml of distilled water) Meat extract 5 g, peptone 10 g, sodium chloride 5 g, agar 15 g.

[(Cultural conditions]

The medium is set on sterilized dishes and streak culture is performed. 37° C.×1 day.

[Observation parameter]

Presence of catalase: The presence of the enzyme which catalyzes the decomposition of hydrogen peroxide. One drop of 3% $H_2O_2$ solution is placed on a glass slide and a loopful of the test organism is thoroughly mixed therein. Positive test: copious or sustained formation of oxygen bubbles.

TABLE 4

Physiological characters (1)

| | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| (1) Reduction of nitrate | Positive | Positive | Positive |
| (2) Denitrification reaction | Negative | Negative | Negative |
| (3) VP test | Positive | Positive | Positive |
| (4) NR test | Negative | Negative | Negative |
| (5) Production of indole | Negative | Negative | Negative |
| (6) Production of hydrogen sulfide | Negative | Negative | Negative |
| (7) Hydrolysis of starch | Positive | Positive | Positive |
| (8) Liquefaction of casein | Positive | Positive | Positive |
| (9) Utilization of citric acid | Positive | Positive | Positive |
| (10) Production of pigments | Negative | Negative | Negative |
| (11) Urease | Negative | Negative | Negative |
| (12) Oxidase | Positive | Positive | Positive |
| (13) Catalase | Positive | Positive | Positive |

4. Physiological Characters (2) (Results are Shown below in Table 5 and Table 6)

(1) pH-dependent Growth

[Medium composition] (commercial nutrient broth, in 1,000 ml of distilled water) Meat extract 3 g, peptone 5 g, pH control agent (acid: $H_2SO_4$ 1 ml/100 ml; alkali: NaOH 4 g/1,000 ml). The pH is varied in 15 steps between 3.6 and 10.9.

[Cultural conditions]

The medium is dispensed into sterile test tubes and a loopful of the test organism is suspended in the medium. 37° C.×1 day, under shaking at 170 cycles/min.

[Observation parameter]

Growth

++ . . . Good growth

+ . . . Moderate growth

−+ . . . Slight growth

− . . . Scanty growth

−− . . . No growth at all (2) Temperature-dependent Growth

[Medium composition] (commercial broth agar medium, in 1,000 ml of distilled water) Meat extract 5 g, sodium chloride 5 g, peptone 10 g, agar 15 g (pH 7.0±0.1).

[Cultural conditions]

The medium is set on sterilized dishes and streak culture is performed.

The temperature is varied serially, 4, 10, 20, 30, 37, 40 and 50° C., each×1 day.

[Observation parameter]

Growth

++ . . . Good growth

+ . . . Moderate growth

−+ . . . Slight growth

− . . . Scanty growth

−− . . . No growth at all (3) Attitude Toward Oxygen

[Medium composition] (commercial broth agar medium, in 1,000 ml of distilled water) Meat extract 5 g, sodium chloride 5 g, peptone 10 g, agar 15 g (pH 7.0±0.1).

[Cultural conditions]

The test organism and the medium are mixed and set in a high layer in sterilized test tubes and incubated. 37° C.×1 day.

[Observation parameter]

Growth under aerobic/anaerobic conditions

Growth exclusively on surface

. . . aerobic

Growth on surface and in substance

. . . facultatively anaerobic

Growth exclusively in substance

. . . oligatively anaerobic (4) O-F Test

[Medium composition] (in 1,000 ml of distilled water) Peptone 2 g, sodium chloride 5 g, $K_2HPO_4$ 0.3 g, agar 3 g, 0.2% BTB 15 ml, glucose 10 g (Note: glucose is sterilized with a bacterial filter and the other components are sterilized by autoclaving at 121° C.×15 min.).

[Cultural conditions]

The medium is distributed and set in a high layer in 2 sterilized test tubes. The test organism is stab-cultured in each tube. The medium in one tube is overlayed with liquid paraffin in a thickness of 1~2 cm. 37° C.×3–4 days.

[Observation parameter]

Oxidative or fermentative glycolysis

"O" . . . oxidative glycolysis (yellowing under anaerobic conditions only)

"F" . . . fermentative glycolysis (yellowing under both aerobic and anaerobic conditions)

(5) PPA Test

[Medium composition] (in 1,000 ml of distilled water) Yeast extract 3 g, phenylalanine 2 g, sodium phosphate 1 g, sodium chloride 5 g, agar 15 ml.

[Cultural conditions]

The medium is set in an inclined position in sterilized test tubes and smear culture is performed. 37° C.×1 day.

[Observation parameter]

Deamination of phenylalanine to phenylpyruvic acid: a 10% aqueous solution of ferric chloride is dripped. Positive test: change of color to green.

(6) Utilization of Propionic Acid

[Medium composition] (in 1,000 ml of distilled water) Magnesium sulfate 0.2 g, sodium propionate 2 g, dipotassium hydrogenphosphate 1 g, monoammonium phosphate 1 g, sodium chloride 5 g, agar 10 g, 0.2% BTB solution 12 ml.

[Cultural conditions]

The medium is set in sterilized dishes and streak culture is performed. 37° C.×1 day.

[Observation parameter]

Growth by utilizing propionic acid as a sole carbon source: Positive test: change of medium color to blue or growth of the organism (7) Decomposition of Tyrosine

[Medium composition] (in 1,000 ml of distilled water) L-tyrosine 5 g, meat extract 3 g, peptone 5 g, agar 15 g (Note: tyrosine and nutrient agar are separately steam-sterilized and mixed).

[Cultural conditions]

The medium is set in sterilized dishes and streak culture is performed. 37° C.×7~14 days.

[Observation parameter]

Decomposition of tyrosine: Positive test: dissolution of crystalline tyrosine beneath the colony.

(8) Egg Yolk Reaction

[Medium composition] (in 1,000 ml of distilled water) Peptone 10 g, $Na_2HPO_4$, 5 g, $KH_2PO_4$ 1 g, NaCl 12 g, MgSO$_4$ 0.1 g, glucose 2 g, egg yolk 15 ml (Note: the components other than egg yolk are steam-sterilized, the egg yolk is aseptically aspirated and added, and the mixture is ripened in the refrigerator for 24 hours. The broth not containing egg yolk is also provided)

[Cultural conditions]

The above media with and without egg yolk are dispensed into 2 sterilized test tubes and a loopful of the test organism is suspended in each medium. 37 ° C.×7 days. Observation is made on days 1, 3, 5 and 7. Shake culture at 170 cycles/min.

[Observation parameter]

Occurrence of white precipitates: Positive test: white precipitates in the lower part of the tube and on the surface of the medium in the presence of egg yolk in contrast to the absence of egg yolk.

(9) Growth in the Presence of 2% NaCl

[Medium composition] (in 1,000 ml of distilled water) Meat extract 3 g, peptone 5 g, NaCl 120 g.

[Cultural conditions]

The medium is dispensed into sterilized test tubes and a loopful of the test organism is suspended in the medium. 37° C.×14 days, under shaking at 170 cycles/min.

[Observation parameter]

Growth

++ . . . Good growth

+ . . . Moderate growth

−+ . . . Slight growth

− . . . Scanty growth

−− . . . No growth at all

(10) Growth in the Presence of 5% NaCl

(11) Growth in the Presence of 7% NaCl

(12) Growth in the Presence of 12% NaCl

(13) Growth in the Presence of 20% NaCl

[Medium composition] (in 1,000 ml of distilled water)

The amount of NaCl in the above medium composition for (9) is altered to 70 g, 120 g and 200 g.

[Cultural conditions]

The same as for (9).

[Observation parameter]

The same as for (9).

(14) Growth in the Presence of Lysozyme

[Medium composition] (in 1,000 ml of distilled water) Meat extract 3 g, peptone 5 g, lysozyme 0.1 g (lysozyme is boiled in 0.01-N HCl for 20 min. and added to nutrient broth).

[Cultural conditions]

The medium is dispensed into sterilized test tubes and a loopful of the test organism is suspended in the medium. 37° C.×14 days, under shaking at 170 cycles/min.

[Observation parameter]

Growth:

++ . . . Good growth

+ . . . Moderate growth

−+ . . . Slight growth

− . . . Scanty growth

−− . . . No growth at all

(15) Production of Hemolysin

[Medium composition] (commercial sheep blood agar medium, in 1,000 ml of distilled water)

Pancreatic digest of casein 14.5 g, papaic digest of soybean meal 5.0 g, sodium chloride 5.0 g, growth factors 1.5 g, agar 14.0 g, sheep blood, defibrinated 5.0%.

[Cultural conditions]

The medium is set in sterilized dishes and streaked with the test organism. 37° C.×1 day.

[Observation parameter]

Production of Hemolysin

α-hemolysis . . . a green zone around the colony (denaturation of hemoglobin)

β-hemolysis . . . a transparent zone around the colony (disruption of red blood cell membrane)

TABLE 5

| Physiological characters (2) | | | |
|---|---|---|---|
| | Bacillus sp. OYK-01-600 (FERM BP-6394) | Bacillus sp. OYK-03-600 (FERM BP-6395) | Bacillus sp. OYK-04-000 (FERM BP-6396) |
| (1) pH-dependent growth | | | |
| pH 3.6 | − − | − − | − − |
| pH 4.1 | − − | − − | − − |
| pH 4.5 | − − | − − | − − |
| pH 4.9 | − − | − − | − − |
| pH 5.4 | − | − | − |
| pH 6.1 | + + | + + | + + |
| pH 6.5 | + + | + + | + + |
| pH 7.1 | + + | + + | + + |
| pH 7.5 | + + | + + | + + |
| pH 3.0 | + + | + + | + + |
| pH 5.6 | + + | + + | + + |
| pH 9.1 | + | + | + + |
| pH 9.5 | + | + | + |
| pH 10.2 | + | + | + |
| pH 10.9 | − + | − + | − + |
| (2) Temperature-dependent growth | | | |
| 4° C. | − − | − − | − − |
| 10° C. | − + | − + | − + |
| 20° C. | + | + | + |
| 30° C. | + + | + + | + + |
| 37° C. | + + | + + | + + |
| 40° C. | + + | + + | + + |
| 50° C. | + | + | + |

TABLE 6

| | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| (3) Attitude toward oxygen | Facultatively anaerobic | Facultatively anaerobic | Facultatively anaerobic |
| (4) O-F test | F | F | F |
| (5) PPA test | Negative | Negative | Negative |
| (6) Utilization of propionic acid | Negative | Negative | Negative |
| (7) Decomposition of tyrosine | Negative | Negative | Negative |
| (8) Egg yolk reaction | Negative | Negative | Negative |
| (9) Growth in the presence of 2% NaCl | + + | + + | + + |
| (10) Growth in the presence of 7% NaCl | + | − | + |
| (11) Growth in the presence of 7% NaCl | − | − − | − − |
| (12) Growth in the presence of 12% NaCl | − − | − − | − − |
| (13) Growth in the presence of 20% NaCl | − − | − − | − − |
| (14) Growth in the | | | |

TABLE 6-continued

| | Bacillus sp. OYK-01-600 (FERM BP-6394) | Bacillus sp. OYK-03-600 (FERM BP-6395) | Bacillus sp. OYK-04-000 (FERM BP-6396) |
|---|---|---|---|
| presence of lysozyme | ++ | ++ | ++ |
| (15) Production of hemolysin | Negative | Negative | Negative |

5. Production of Acid and Gas from Carbon Sources (Results are Shown below in Table 7)

(1) D-glucose

[Medium composition] (in 1,000 ml of distilled water) Peptone 1 g, sodium chloride 5 g, agar 10 g, 0.2% BTB 15 ml, D-glucose 8 g.

[Cultural conditions]

The medium is dispensed into sterilized test tubes and set in a high layer. Then, stab culture is performed. 37° C.×14 day.

[Observation parameter]

Production of acid: evaluated according to the degree of yellowing of BTB reagent ++ . . . Copious production
+ . . . Moderate production
−+ . . . Mild production
− . . . No production Production of gas: evaluated according to cracks in the high layer ++ . . . Copious production
+ . . . Moderate production
−+ . . . Mild production
− . . . No production (2) L-arabinose
(3) D-xylose
(4) D-mannit
(5) D-mannose
(6) D-galactose
(7) D-sorbitose
(8) Inositol
(9) Trehalose
(10) Lactose
(11) Maltose
(12) Fructose

[Medium composition] (in 1,000 ml of distilled water)

The carbohydrate (D-glucose) in the above-mentioned recipe for (1) is replaced with the carbohydrates (2)~(12).

[Cultural conditions]

The same as for (1).

[Observation parameters]

The same as for (1).

TABLE 7

Production of acid and gas from carbon sources

| | Bacillus sp. OYK-01-600 (FERM BP-6394) | | Bacillus sp. OYK-03-600 (FERM BP-6395) | | Bacillus sp. OYK-04-000 (FERM BP-6396) | |
|---|---|---|---|---|---|---|
| | Acid | Gas | Acid | Gas | Acid | Gas |
| (1) D-glucose | ++ | − | ++ | − | ++ | − |
| (2) L-arabinose | ++ | − | ++ | − | ++ | − |
| (3) D-xylose | + | − | + | − | + | − |

TABLE 7-continued

Production of acid and gas from carbon sources

| | Bacillus sp. OYK-01-600 (FERM BP-6394) | | Bacillus sp. OYK-03-600 (FERM BP-6395) | | Bacillus sp. OYK-04-000 (FERM BP-6396) | |
|---|---|---|---|---|---|---|
| | Acid | Gas | Acid | Gas | Acid | Gas |
| (4) D-mannit | + | − | + | − | + | − |
| (5) D-mannose | −+ | − | −+ | − | −+ | − |
| (6) D-galactose | − | − | − | − | − | − |
| (7) D-sorbitose | − | − | − | − | − | − |
| (8) Inositol | + | − | + | − | + | − |
| (9) Trebalose | + | − | + | − | + | − |
| (10) Lactose | −+ | − | −+ | − | −+ | − |
| (11) Maltose | − | − | − | − | − | − |

6. Identification Results

The three strains OYK-01-600, OYK-03-600 and OYK-04-000 were classified according to the following literature.

(1) Bergey's Mannual of Determinative Bacteriology, Vol. 2 (1986), Williams & Wilkins U.S.A.

(2) R. E. Gordon, W. C. Haynes, C. H. Pang. (1973), The Genus Bacillus. Agr. Handbook No. 427, United States Department of Agriculture, Washington D.C.

TABLE 8

Identification results (1)-Generic differentiation

| | Bacillus | OYK-01-600 | OYK-03-600 | OYK-04-000 |
|---|---|---|---|---|
| (1) Rods | + | + | + | + |
| (2) Diameter ≧ 2.5 μm | − | − | − | − |
| (3) Filaments | − | − | − | − |
| (4) Curvature of rods or filaments | − | − | − | − |
| (5) Coal in tetrads or packets | − | − | − | − |
| (6) Endospore formation | + | + | + | + |
| (7) Motility | + | + | + | + |
| (8) Positive Gram-stain in growth phase | + | + | + | + |
| (9) Obligatory aerobic | D | − | − | − |
| (10) Facultatively anaerobic or microaerophilic | D | + | + | + |
| (11) Anaerobia | − | − | − | − |
| (12) Fermentation of homo-lactic acid | D | + | + | + |
| (13) Reduction of sulfate | − | − | − | − |
| (14) Catalase | + | + | + | + |
| (15) Oxidase | D | + | + | + |
| (16) Production of acid from glucose | + | + | + | + |
| (17) Reduction of nitrate | D | + | + | + |
| (18) Mol % G + C | 32–69 | ND | ND | ND |

+: 90% or more of strains are positive
−: 10% or less of strains are positive
D: dependent on species
ND: Not determined

TABLE 9

Identification results (2)-Specific differentiation

| | subtilis | firmus | pumilus | licheniformis | lentus | OYK-01-600 | OYK-03-600 | OYK-04-000 |
|---|---|---|---|---|---|---|---|---|
| 1) Cell diameter ≧ 1.0 μm | − | − | − | − | − | − | − | − |
| 2) Spherical spores formed | − | − | − | − | − | − | − | − |
| 3) Extends sporangium | − | − | − | − | − | − | − | − |
| 4) Parasporal crystals | − | − | − | − | − | − | − | − |
| 5) Catalase | + | + | + | + | + | + | + | + |
| 6) Growth under anaerobic conditions | − | − | − | + | − | + | + | + |
| 7) Voges-Proskauer test | + | − | + | + | − | + | + | + |
| 8) Growth in VP broth | | | | | | | | |
| pH <6 | d | − | + | + | − | d | d | d |
| pH >7 | − | − | − | − | ND | + | + | + |
| 9) Production of acid from carbohydrates: | | | | | | | | |
| D-glucose | + | + | + | + | + | + | + | + |
| L-arabinose | + | − | + | + | + | + | + | + |
| D-xylose | + | − | + | + | + | d | d | d |
| D-mannitol | + | + | + | + | + | d | d | d |
| 10) production of gas from glucose | − | − | − | − | − | − | − | − |
| 11) Hydrolysis: | | | | | | | | |
| Casein | + | + | + | + | d | + | + | + |
| Gelatin | + | + | + | + | d | + | + | + |
| Starch | + | + | − | + | + | + | + | + |
| 12) Utilization of acid as C source: | | | | | | | | |
| Citric acid | + | − | + | + | − | + | + | + |
| Propionic acid | − | − | − | + | − | − | − | − |
| 13) Decomposition of tyrosine | − | d | − | − | − | − | − | − |
| 14) Deamination of phenylalanine | − | d | − | − | d | − | − | − |
| 15) Egg yolk reaction | − | − | − | − | − | − | − | − |
| 16) Nitrate reduced to nitrite | + | d | − | + | d | + | + | + |
| 17) Production of indole | − | − | − | − | − | − | − | − |

TABLE 10

| | subtilis | firmus | pumilus | licheniformis | lentus | OYK-01-600 | OYK-03-600 | OYK-04-000 |
|---|---|---|---|---|---|---|---|---|
| 18) Production of dihydroxyacetone | ND | − | ND | ND | − | ND | ND | ND |
| 19) Requirement for NaCl and KCl | − | − | − | − | − | − | − | − |
| 20) Requirement for allantoin or urate | − | − | − | − | − | − | − | − |
| 21) Growth in nutrient broth, pH 6.8 | + | + | + | + | + | + | + | + |
| 22) Growth in nutrient broth, pH 5.7 | + | − | + | + | − | d | d | d |
| 23) Growth in NaCl broth: | | | | | | | | |
| 2% | + | + | + | + | WD | + | + | + |
| 5% | + | + | + | + | ND | d | − | d |
| 7% | + | + | + | + | d | d | − | − |
| 10% | ND | ND | ND | ND | ND | − | − | − |
| 24) Temperature for growth: | | | | | | | | |
| 5° C. | − | − | − | − | ND | − | − | − |
| 10° C. | d | d | + | − | ND | d | d | d |
| 30° C. | + | + | + | + | + | + | + | + |
| 40° C. | + | + | + | + | ND | + | + | + |
| 50° C. | d | − | d | + | − | d | d | d |
| 55° C. | − | − | − | + | − | − | − | − |
| 60° C. | − | − | − | − | − | − | − | − |
| 25) Growth in the presence of lysozyme | d | − | d | d | − | + | + | + |
| 26) Grows on $H_2+CO_2$ or CO as carbon source | − | − | − | − | − | − | − | − |

+: 90% or more of strains are positive
−: 90% or more of strains are negative
d: 11–89% of strains are positive
ND: not determined From Table 8, the above three strains are invariably considered to belong to the genus Bacillus, and from Tables 9 and 10, they are considered to be organisms related to *B. subtilis*. However, in view of the fact that they grow under anaerobic conditions, that the production of acid from carbohydrates is weak, and that they do not grow in 7% NaCl broth, they could not be identified with *B. subtilis* but were considered to be neotypes and each designated as Bacillus sp.

[Reference to the deposited biological materials]
(1) Name of the deposit organization: Patent Microorganism Deposit Center, National Institute of Bioscience and Human Technology, Agency of Industrial Science and Technology, MITI, Japan. Address: Postal zone 305-0046 Higashi 1-1-3, Tsukuba-shi, Ibaraki, Japan (Tel. 0298-54-6029)
(2) Date of deposit: Jun. 29, 1998
(3) Accession Nos.:
  1) FERM BP-6394
  2) FERM BP-6395
  3) FERM BP-6396

C. Growth Velocity Test with the OYK Organism
(FIG. 1)

The novel microorganism of the present invention begins to grow quickly after the start of culture without requiring an induction period (acclimatization period for proliferation). For example, under the cultural conditions of 20~40° C., the initial concentration of about $10^3$ cells/ml (g) increases to not less than $10^8$ cells/ml (g) within 6 hours.

FIG. 1 shows the time course of growth of Bacillus sp. OYK-01-600. As control, the time course of growth of the type culture of *B. subtilis* (IFO 3134) is also shown. The growth curves in FIG. 1 were constructed by plotting the logarithm of the number of bacterial cells on the ordinate against time on the abscissa. It will be apparent if only from the graph that the OYK strain of the invention has substantially no induction period but begins to multiply rapidly, with the initial concentration of about $10^3$ cells/g reaching a concentration of $10^8$ cells/ml or more in about 5 hours. In contrast, the type culture of *B. subtilis* (IFO 3134) begins to grow after an induction period of 6~8 hours following the start of culture and it took about 12 hours for the organism to multiply to the concentration of about $10^8$ cells/g. On the other hand, the OYK strain is 4 times as large in volume as said type culture strain, and whereas the volume multiple of the type culture strain was 6 after 4 hours, that of the OYK strain was 20,000. Thus, in terms of volume, the magnitude of increase was 20,000×4=80,000 times. By simple comparison, the volume occupied by the present strain is 80,000÷6=13,333 . . . , or more than 10,000 times as large.

What is claimed is:

1. An isolated strain of *Bacillus subtilis* which is at least one member selected from the group consisting of Bacillus sp. OYK-01-600 (FERM BP-6394), Bacillus sp. OYK-03-600 (FERM BP-6395) and Bacillus sp. OYK-04-000 (FERM BP-6396).

2. An isolated strain of *Bacillus subtilis* according to claim 1 having a proliferation rate wherein a first population of $10^3$ cells/ml yields a second population of not less than $10^7$ cells/ml after 4 hours when it is subjected to nutrient broth shake culture at 37° C.

* * * * *